US011061222B2

(12) United States Patent
Ogata (10) Patent No.: US 11,061,222 B2
(45) Date of Patent: Jul. 13, 2021

(54) OPTICAL FIBER SCANNING APPARATUS AND ENDOSCOPE

(71) Applicant: OLYMPUS CORPORATION, Tokyo (JP)

(72) Inventor: Masanori Ogata, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/451,785

(22) Filed: Jun. 25, 2019

(65) Prior Publication Data

US 2019/0317316 A1    Oct. 17, 2019

Related U.S. Application Data

(63) Continuation of application No. PCT/JP2016/088694, filed on Dec. 26, 2016.

(51) Int. Cl.
*H04N 5/225* (2006.01)
*G02B 26/10* (2006.01)
(Continued)

(52) U.S. Cl.
CPC .............. *G02B 26/103* (2013.01); *A61B 1/07* (2013.01); *G02B 6/0006* (2013.01);
(Continued)

(58) Field of Classification Search
CPC ...... A61B 1/07; G02B 23/2469; G02B 26/10; G02B 26/103; G02B 6/0006; G02B 6/0008; H04N 2005/2255; H04N 5/2256
See application file for complete search history.

(56) References Cited

U.S. PATENT DOCUMENTS 6,294,775 B1 *  9/2001  Seibel .................. A61B 1/0008
                                                   250/208.1
2008/0161648 A1 *  7/2008  Karasawa ............ A61B 1/0017
                                                        600/182
(Continued)

FOREIGN PATENT DOCUMENTS

EP           2 952 949 A1    12/2015
JP         2008-116922 A     5/2008
(Continued)

OTHER PUBLICATIONS

International Search Report dated Feb. 14, 2017 received in PCT/JP2016/088694.

*Primary Examiner* — Md N Haque
(74) *Attorney, Agent, or Firm* — Scully, Scott, Murphy & Presser, P.C.

(57) ABSTRACT

An optical fiber scanning apparatus includes an optical fiber whose fixed end is fixed and a free end for emitting illumination light of which vibrates in a first direction (X-axis direction) and a second direction (Y-axis direction), a ferrule including a through hole through which the optical fiber is inserted and including a pair of first fixing sections and a pair of second fixing sections which respectively fix the fixed end of the optical fiber, and piezoelectric elements or a magnet configured to vibrate the optical fiber, in which the optical fiber is sandwiched between the pair of first fixing sections and fixed in the first direction, and is sandwiched between the pair of second fixing sections and fixed in the second direction, and the pair of first fixing sections and the pair of second fixing sections differ in a shape of an abutment portion abutting on the optical fiber.

12 Claims, 7 Drawing Sheets

(51) Int. Cl.
*A61B 1/07* (2006.01)
*F21V 8/00* (2006.01)
*G02B 23/24* (2006.01)

(52) U.S. Cl.
CPC ....... *G02B 6/0008* (2013.01); *G02B 23/2469* (2013.01); *H04N 5/2256* (2013.01); *H04N 2005/2255* (2013.01)

(56) References Cited

U.S. PATENT DOCUMENTS

| | | | | |
|---|---|---|---|---|
| 2014/0114131 | A1* | 4/2014 | Sakai | G02B 26/103 |
| | | | | 600/182 |
| 2014/0232993 | A1* | 8/2014 | Kim | H04N 9/3129 |
| | | | | 353/31 |
| 2016/0025966 | A1* | 1/2016 | Shimamoto | G02B 6/3636 |
| | | | | 359/199.4 |

FOREIGN PATENT DOCUMENTS

| | | | |
|---|---|---|---|
| JP | 2014-044265 A | | 3/2014 |
| JP | 2014-145937 A | | 8/2014 |
| JP | 2015-232493 A | | 12/2015 |
| JP | 2015232493 | * | 12/2015 |
| WO | 2014/119300 A1 | | 8/2014 |
| WO | 2015/190498 A1 | | 12/2015 |

\* cited by examiner

OPTICAL FIBER SCANNING APPARATUS AND ENDOSCOPE

CROSS REFERENCE TO RELATED APPLICATION

This application is a continuation application of PCT/JP2016/088694 filed on Dec. 26, 2016, the entire contents of which are incorporated herein by this reference.

BACKGROUND OF INVENTION

1. Field of the Invention

The present invention relates to an optical fiber scanning apparatus including an optical fiber a free end of which vibrates in a first direction and a second direction perpendicular to the first direction, and an endoscope including the optical fiber scanning apparatus in a distal end portion of an insertion section.

2. Description of the Related Art

An image pickup apparatus using an image pickup device such as a CCD or a CMOS image sensor simultaneously receives reflected light from a subject using many light receiving elements arranged in a matrix shape, to acquire an object image. In an endoscope which shoots a dark inside of a body, an image in a range illuminated with light from a light source is acquired.

On the other hand, an optical scanning type image pickup apparatus sequentially receives, while scan-irradiating an object with a light spot, reflected light from the object, to generate an object image based on data representing the received light.

For example, the optical scanning type image pickup apparatus performs the scanning irradiation with the light spot when an optical fiber scanning apparatus vibrates a free end in a distal end portion of an optical fiber in a cantilevered state which guides light from a light source to perform two-dimensional scanning.

Examples of means for vibrating the optical fiber include a piezoelectric driving method for attaching a piezoelectric element to an optical fiber and vibrating the piezoelectric element disclosed in U.S. Pat. No. 6,294,775 and an electromagnetic driving method for vibrating a permanent magnet attached to an optical fiber using an electromagnetic coil disclosed in Japanese Patent Application Laid-Open Publication No. 2008-116922. If the optical fiber is vibrated, when the optical fiber is vibrated in the vicinity of a resonance frequency of the optical fiber, a large deflection (displacement or amplitude) of the optical fiber is obtained with small energy.

To cause the free end of the optical fiber to scan two-dimensionally, X-axis direction scanning and Y-axis direction scanning perpendicular to the X-axis direction need to be independently controlled. However, if both the scannings have the same resonance frequency, even when the free end of the optical fiber is scanning in the X-axis direction, for example, the free end of the optical fiber also unintentionally scans in the Y-axis direction. Thus, a distortion may occur in a scan trajectory.

Japanese Patent Application Laid-Open Publication No. 2014-44265 discloses an optical scanning apparatus which includes an optical fiber having different resonance frequencies, respectively, in an X-axis direction and a Y-axis direction and performs stable scanning irradiation.

SUMMARY OF THE INVENTION

An optical fiber scanning apparatus according to an aspect of the present invention includes an optical fiber a fixed end of which is fixed and a free end for emitting illumination light of which vibrates in a first direction and a second direction perpendicular to the first direction, a ferrule including a through hole through which the optical fiber is inserted and including a pair of first fixing sections and a pair of second fixing sections which respectively fix the fixed end of the optical fiber, and piezoelectric elements or a magnet configured to vibrate the optical fiber, in which the optical fiber is sandwiched between the pair of first fixing sections and fixed in the first direction, and is sandwiched between the pair of second fixing sections and fixed in the second direction, and the pair of first fixing sections and the pair of second fixing sections differ in a shape of an abutment portion abutting on the optical fiber.

An endoscope according to another aspect of the present invention includes an optical fiber scanning apparatus in a distal end portion of an insertion section, the optical fiber scanning apparatus including an optical fiber a fixed end of which is fixed and a free end for emitting illumination light of which vibrates in a first direction and a second direction perpendicular to the first direction, a ferrule including a through hole through which the optical fiber is inserted and including a pair of first fixing sections and a pair of second fixing sections which respectively fix the fixed end of the optical fiber, and piezoelectric elements or a magnet configured to vibrate the optical fiber, in which the optical fiber is sandwiched between the pair of first fixing sections and fixed in the first direction, and is sandwiched between the pair of second fixing sections and fixed in the second direction, and the pair of first fixing sections and the pair of second fixing sections differ in a shape of an abutment portion abutting on the optical fiber.

DETAILED DESCRIPTION OF THE PREFERRED EMBODIMENTS

First Embodiment

An embodiment of the present invention will be described below with reference to the drawings.

Figure 1:
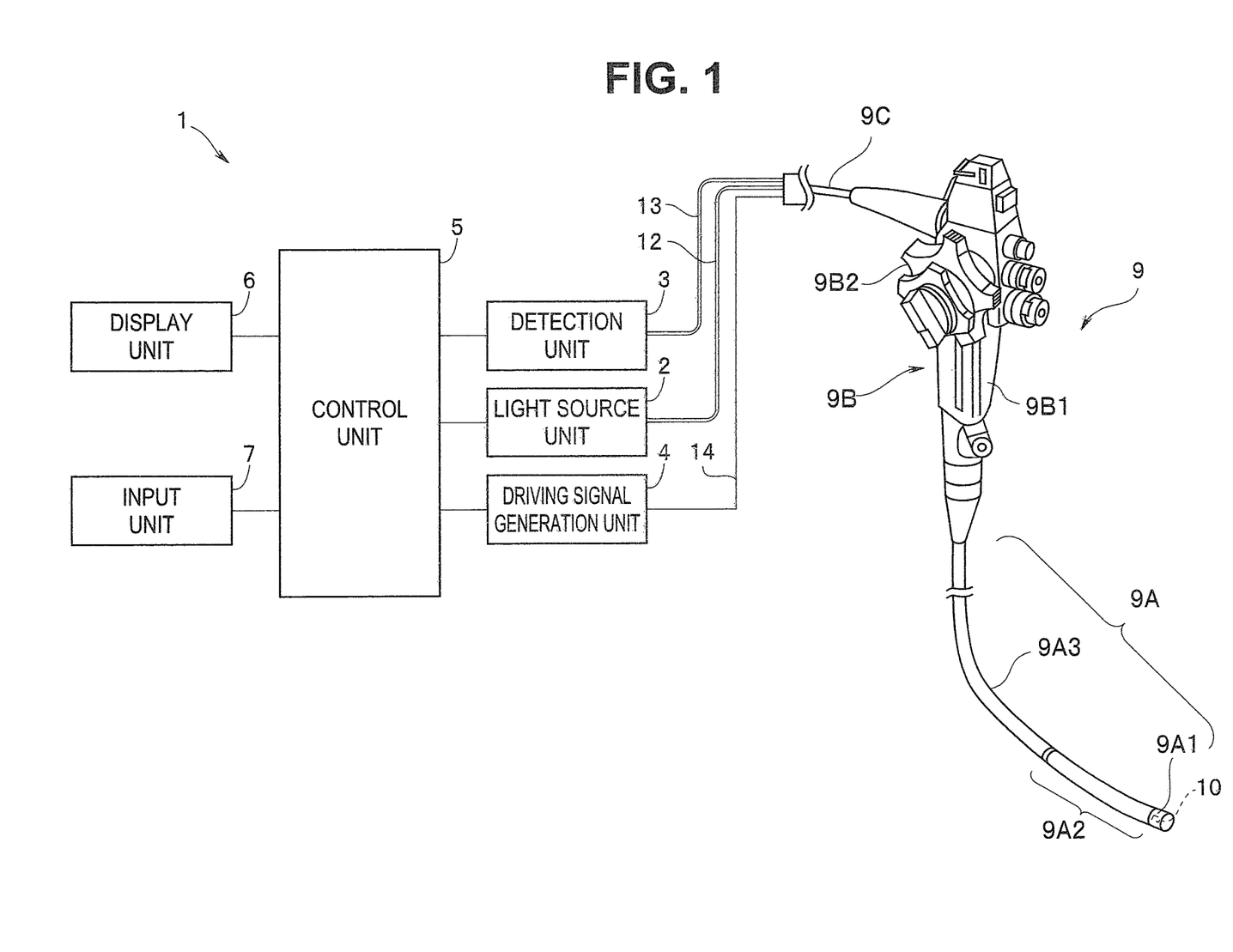
FIG. 1 is a configuration diagram of an endoscope system including an optical fiber endoscope according to a first embodiment.

As illustrated in FIG. 1, an endoscope 9 in which an optical fiber scanning apparatus 10 is disposed, together with a light source unit 2, a detection unit 3, a driving signal generation unit 4, a control unit 5, a display unit 6, and an input unit 7, constitutes an endoscope system 1.

In the following description, it should be noted that the drawings based on each of embodiments are schematic, and a relationship between a thickness and a width of each of sections, a ratio of thicknesses of the sections, and the like respectively differ from actual ones, and the sections which also differ in a dimensional relationship and a ratio among the drawings may be included. Illustration of some of components and assignment of reference numerals may be omitted.

The endoscope 9 includes an elongated insertion section 9A to be inserted into a living body, an operation section 9B, and a universal cable 9C. The insertion section 9A in the endoscope 9 includes a distal end portion 9A1, a bending portion 9A2, and a flexible tube portion 9A3. Note that the endoscope 9 according to the embodiment is a so-called flexible endoscope, but the endoscope 9 may be a so-called rigid endoscope in which the insertion section 9A is rigid and may be used for medical and industrial purposes.

In the operation section 9B, a bending operation knob 9B2 for performing a bending operation for the bending portion 9A2 is turnably disposed. A connection section between the insertion section 9A and the operation section 9B is a grasping section 9B1 to be grasped by a user.

An optical fiber 12 for illumination, an optical fiber 13 for light receiving, a signal line 14 configured to transmit a driving signal from the driving signal generation unit 4 to a driving section 25 (see FIG. 2), and the like are inserted through the universal cable 9C and the insertion section 9A and are connected to the optical fiber scanning apparatus 10 disposed in the distal end portion 9A1.

The light source unit 2 multiplexes respective light beams from three laser light sources each configured to emit CW (consecutive oscillation) laser light in three primary colors, e.g., red, green, and blue, and emits the multiplexed light beams as white light. Examples of the laser light source which can be used include a DPSS (diode pumped solid state) laser and a laser diode. Needless to say, a configuration of the light source unit 2 is not limited to this. Examples of the light source unit 2 may include a light source unit using one laser light source and a light source unit using other plurality of light sources.

When a distal end portion as a cantilever of the optical fiber 12 vibrates by the driving section 25, spot illumination light to be emitted by the optical fiber 12 scans two-dimensionally to illuminate an object to be observed, as described below. Reflected light from the object to be observed illuminated with the illumination light enters the detection unit 3 via the optical fiber 13 for detection. The detection unit 3 decomposes the reflected light into spectral components, and converts the spectral components into an electric signal using a photodiode. The control unit 5 synchronously controls the light source unit 2, the detection unit 3, and the driving signal generation unit 4 while processing the electric signal to be outputted by the detection unit 3, to synthesize images and display a composite image on the display unit 6. The user performs settings of the endoscope system 1, such as a scanning speed and brightness of the displayed image, via the input unit 7.

Note that the light source unit 2, the detection unit 3, the driving signal generation unit 4, and the control unit 5 may be accommodated in the same housing, or may be respectively accommodated in different housings.

As illustrated in FIGS. 2 to 5, the optical fiber scanning apparatus 10 includes a housing 11, optical fibers 12 and 13, a ferrule 20 as a holding section, the driving section 25 including piezoelectric elements configured to vibrate the optical fiber 12, and an illumination optical system 15.

Figure 2:
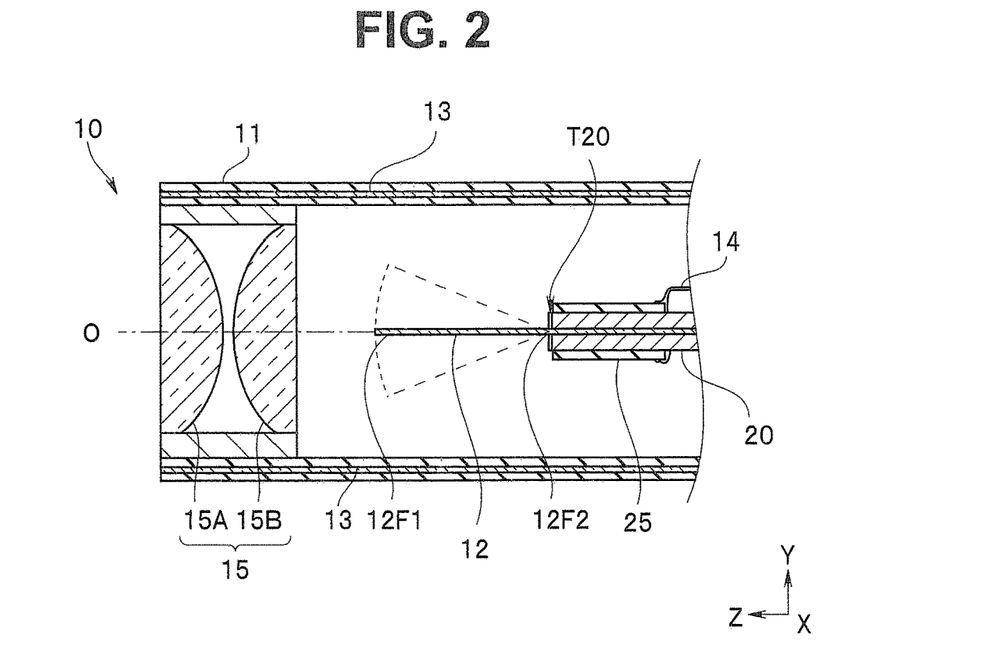
FIG. 2 is a cross-sectional view of an optical fiber scanning apparatus according to the first embodiment.

The optical fiber 12 guides the light from the light source unit 2, and emits illumination light from a free end 12F1. The illumination optical system 15 including a plurality of lenses 15A and 15B is configured to converge the spot illumination light emitted from the optical fiber 12 on a surface of the object to be observed. Note that the illumination optical system 15 is not limited to a two-element lens, but may include one lens or three or more lenses.

The optical fiber 13 for detection may have a light-converging optical system disposed at its distal end. Note that the optical fiber scanning apparatus 10 includes a plurality of optical fibers 13 to obtain a sufficient amount of detected light.

The ferrule 20 composed of nickel, for example, includes a through hole H20 having an opening on a distal end surface 20SA. An inner diameter of the through hole H20 is slightly larger than an outer diameter of the optical fiber 12. For example, the inner diameter of the through hole H20 is more than 100% and not more than 105% of the outer diameter of the optical fiber 12. The optical fiber 12 inserted into the through hole H20 is a cantilever to which a fixed end 12F2 is fixed and which is held along a central axis (optical axis) O in a long-axis direction (Z-axis direction) of the housing 11. The optical fiber 12 is fixed not to move in the optical axis direction (Z-axis direction) with an adhesive or a solder injected from the opening at a rear end of the through hole H20 in the ferrule 20, for example.

The optical fiber 12 constitutes a cantilever in which a distal end portion in a range from the fixed end 12F2 as a starting point to the free end 12F1 vibrates in a first direction (Y-axis direction) and a second direction (X-axis direction) perpendicular to the first direction. The first direction and the second direction are perpendicular to the optical axis direction (Z-axis direction). Note that it goes without saying that the first direction may be the X-axis direction and the second direction may be the Y-axis direction.

The free end 12F1 of the optical fiber 12 moves in a predetermined scanning pattern within an XY plane by a combination of the vibration in the first direction and the vibration in the second direction.

Examples of a scanning method include spiral scanning, raster scanning, and Lissajous scanning depending on a combination of a vibration pattern in the first direction (Y-axis scanning) and a vibration pattern in the second direction (X-axis scanning).

The spiral scanning is performed while spirally changing a diameter by continuously changing a displacement amount in the first direction and a displacement amount in the second direction. The raster scanning is performed by combining low-speed scanning in the first direction and high-speed scanning in the second direction performed during the scanning in the first direction, for example. The Lissajous scanning is performed by combining scanning in the first direction and scanning in the second direction which differ in a driving signal frequency. A difference between the driving signal frequency in the first direction and the driving signal frequency in the second direction is an integer.

In the optical fiber scanning apparatus 10, the driving section 25 configured to vibrate the optical fiber 12 includes piezoelectric elements (piezoelectric ceramics) 25A to 25D respectively disposed on four side surfaces 20SSA to 20SSD of the ferrule 20 as a prism-shaped rectangular parallelepiped. In other words, the pair of piezoelectric elements 25A and 25B configured to drive the optical fiber 12 in an up-and-down direction (Y-axis direction) is disposed on the facing side surfaces 20SSA and 20SSB, and the pair of piezoelectric elements 25C and 25D configured to drive the optical fiber 12 in a right-and-left direction (X-axis direction) is disposed on the facing side surfaces 20SSC and 20SSD.

Note that when a reference numeral denotes each of a plurality of components, one alphabet character at the end of the reference numeral is omitted. For example, each of the piezoelectric elements 25A to 25D is referred to as a piezoelectric element 25.

The piezoelectric element (driving section) 25 expands and contracts when an alternating current driving signal (driving voltage) having a predetermined frequency is applied to the piezoelectric element 25 including piezoelectric elements via the signal line 14. Accordingly, when a Y-axis driving signal is applied to the pair of piezoelectric elements 25A and 25B, the free end 12F1 of the optical fiber 12 vibrates in the first direction (Y-axis direction). When an X-axis driving signal is applied to the pair of piezoelectric elements 25C and 25D, the free end 12F1 of the optical fiber 12 vibrates in the second direction (X-axis direction).

When the control unit 5 controls the driving signal generation unit 4, a driving signal for performing two-dimensional scanning in a predetermined pattern is inputted to the driving section 25. In other words, the X-axis driving signal and the Y-axis driving signal which are controlled such that an irradiation position of the spot illumination light to be irradiated onto the object to be observed draws a trajectory corresponding to a predetermined scanning pattern are inputted to the driving section 25.

As already described, to perform the two-dimensional scanning in the predetermined pattern, the vibration in the X-axis direction and the vibration in the Y-axis direction need to be independently controlled (scanned) at a frequency in the vicinity of a resonance frequency. However, if the optical fiber 12 has a same resonance frequency FR in both the X-axis direction and the Y-axis direction, even when the scanning is being performed in the X-axis direction, for example, the scanning is also unintentionally performed in the Y-axis direction. Thus, a distortion may occur in a scan trajectory.

The resonance frequency FR of the optical fiber 12 is inversely proportional to a square root of a length (vibration length) L of a vibration section from the fixed end 12F2 to the free end 12F1 in primary resonance. In other words, the smaller the vibration length L is, the higher the resonance frequency FR becomes.

Figure 3:
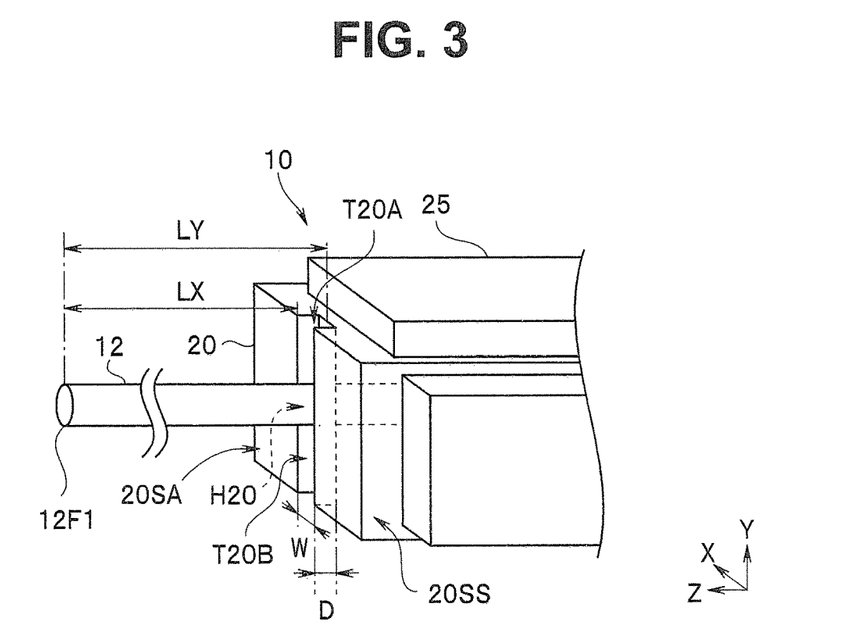
FIG. 3 is a perspective view of a principal part of the optical fiber scanning apparatus according to the first embodiment.

As illustrated in FIG. 3, in the optical fiber scanning apparatus 10, two grooves T20A and T20B respectively extending from both sides in the first direction (Y-axis direction) of the through hole H20 are formed on the distal end surface 20SA of the ferrule 20. A long-axis direction and a depth direction of the grooves T20A and T20B are respectively the first direction (Y-axis direction) and the optical axis direction (Z-axis direction).

The grooves T20A and T20B have a depth D, and a width W of the grooves T20A and T20B is substantially the same as the outer diameter of the optical fiber 12. In the optical fiber 12, a vibration length as a length from the free end 12F1 to the fixed end 12F2 is LY in the Y-axis direction (first direction) and is LX in the X-axis direction (second direction). Accordingly, a resonance frequency FR1 of the vibration in the Y-axis direction (first direction) and a resonance frequency FR2 of the vibration in the Z-axis direction (second direction) of the optical fiber 12 differ from each other.

Figure 4:
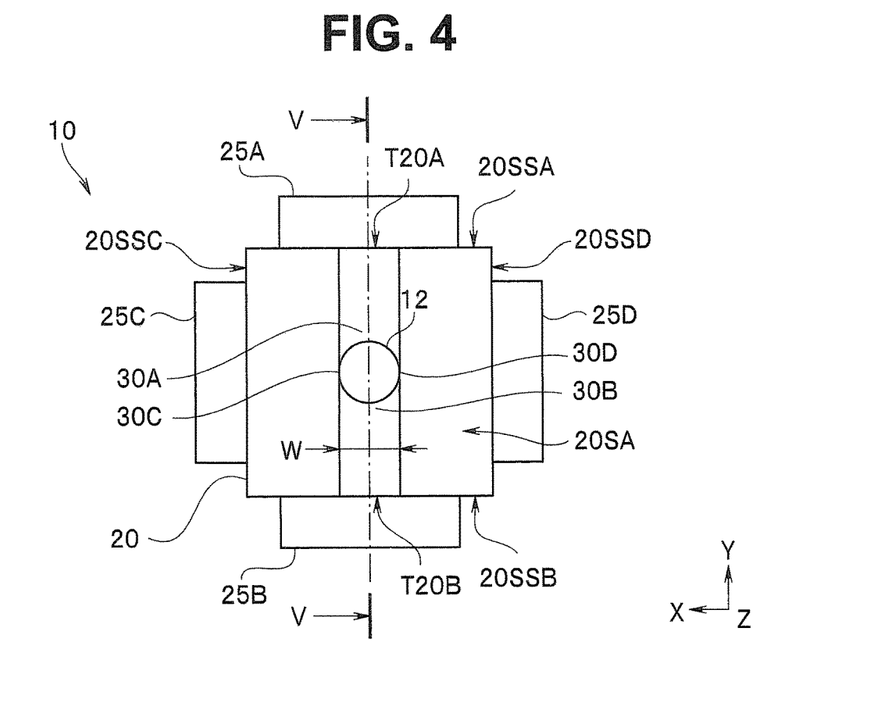
FIG. 4 is a front view of the principal part of the optical fiber scanning apparatus according to the first embodiment.

The optical fiber 12 is considered to be sandwiched between the pair of first fixing sections 30A and 30B in the ferrule 20 and fixed in the first direction (Y-axis direction) and to be sandwiched between the pair of second fixing sections 30C and 30D in the ferrule 20 and fixed in the second direction (X-axis direction).

As already described, the two grooves T20A and T20B each having an opening on a wall surface of the through hole H20 and extending in the first direction (Y-axis direction) are formed on the distal end surface 20SA of the ferrule 20. The grooves T20A and T20B are arranged to face each other on opposite sides of the through hole H20. Thus, the grooves T20A and T20B, together with the through hole H20, apparently constitute a consecutive single groove.

The width W of the groove T20 is substantially the same as the outer diameter of the optical fiber 12. Note that strictly, the width W is slightly larger than the outer diameter of the optical fiber 12, e.g., more than 100% and not more than 105%. The second fixing sections 30C and 30D respectively constitute wall surfaces of the grooves T20. In other words, the second fixing sections 30C and 30D respectively abut on only portions of an entire periphery of an outer peripheral surface of the optical fiber 12. Respective abutment portions of the second fixing sections 30C and 30D on the optical fiber 12 are each in a linear shape parallel to the optical axis direction (Z-axis direction). The second fixing sections 30C and 30D do not prevent the vibration in the first direction (Y-axis direction) of the optical fiber 12.

Note that the width W of the groove T20 is substantially the same as the outer diameter of the optical fiber 12. Thus, the optical fiber 12 can be considered to have respective linear-shaped abutment portions abutting on the grooves T20 when vibrating in the Y-axis direction, although the optical fiber 12 does not always strictly abut on the wall surfaces of the grooves T20.

On the other hand, the optical fiber 12 is fixed in the first direction (Y-axis direction) by the wall surface of the through hole H20 having openings on bottom surfaces of the grooves T20. The first fixing sections 30A and 30B respectively constitute the wall surface, particularly upper and lower walls, which fix the optical fiber 12 in the first direction (Y-axis direction), of the through hole H20. Note that the first fixing sections 30A and 30B abut on the entire periphery of the outer peripheral surface of the optical fiber 12 and also fix the optical fiber 12 in the second direction. In other words, respective abutment portions of the first fixing sections 30A and 30B on the optical fiber 12 are the entire periphery of the outer peripheral surface of the optical fiber 12 and an entire periphery of the wall surface of the through hole H20.

As described above, the first fixing sections 30A and 30B and the second fixing sections 30C and 30D differ in a shape of an abutment surface abutting on the optical fiber 12.

Note that both the first fixing sections 30A and 30B and the second fixing sections 30C and 30D are each a part of the ferrule 20 composed of nickel, and are composed of the same material (nickel). A material for the ferrule 20 is not limited to metal such as nickel if the metal is a rigid material. The ferrule 20 may be composed of ceramic such as zirconia or resin.

Figure 5:
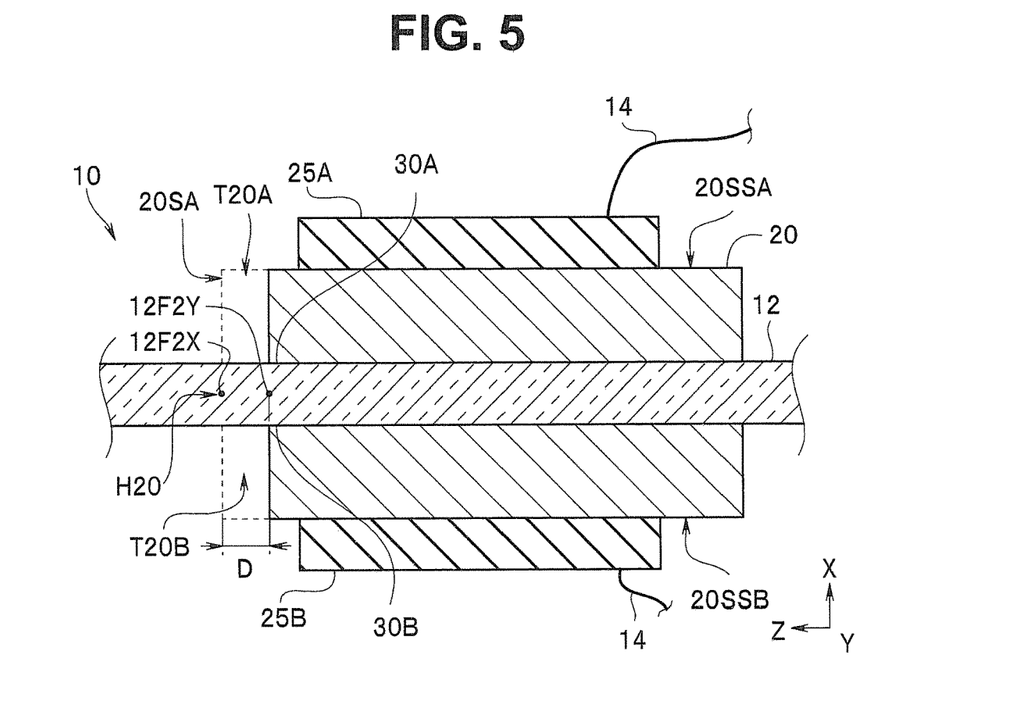
FIG. 5 is a cross-sectional view along a V-V line illustrated in FIG. 4 of the principal part of the optical fiber scanning apparatus according to the first embodiment.

As illustrated in FIG. 5, a fixed end 12F2Y of the vibration in the Y-axis direction of the optical fiber 12 fixed by the first fixing sections 30A and 30B and a fixed end 12F2X of the vibration in the X-axis direction of the optical fiber 12 fixed by the second fixing sections 30C and 30D differ in a position in the optical axis direction (Z-axis direction) by the depth D of the groove T20.

Accordingly, as illustrated in FIG. 3, the length LY from the free end 12F1 to the fixed end 12F2Y of the optical fiber 12 is larger by the depth D of the groove T20 than the length LX from the free end 12F1 to the fixed end 12F2X.

The resonance frequency FR in the front end portion of the optical fiber 12 constituting the cantilever changes depending on a length L from the free end 12F1 to the fixed end 12F2.

Note that the depth D and the length L of the groove T20 are designed depending on a specification. If the outer diameter of the optical fiber 12 is 125 µm, and the length L to the distal end surface 20SA of the ferrule 20, i.e., the length LX to the fixed end 12F2X of the vibration in the X-axis direction from the free end 12F1 is 4 mm, the depth D is 150 µm to 300 µm.

If (LX=4 mm and D=300 µm), the resonance frequency FR1 in the first direction (Y-axis direction) of the optical fiber 12 is 7632 Hz, and the resonance frequency FR2 in the second direction (X-axis direction) is 7688 Hz (tertiary resonance in both the first direction and the second direction). In other words, the resonance frequency FR1 in the first direction in which the length L to the free end 12F1 is larger than LY is lower than the resonance frequency FR2 in the second direction in which the length L is LY. A difference dFR between the resonance frequency FR1 and the resonance frequency FR2 is 56 Hz, and a ratio of the resonance frequency FR1 to the resonance frequency FR2 is 0.7%.

In the optical fiber scanning apparatus 10, the resonance frequency FR1 and the resonance frequency FR2 differ from each other. In the Lissajous scanning, an X-axis driving signal and a Y-axis driving signal can be respectively alternating current signals having substantially the same frequencies as the resonance frequencies in the first direction and the second direction. Accordingly, the optical fiber scanning apparatus 10 can perform stable scanning without a distortion occurring in the scan trajectory.

Note that the through hole H20 is arranged at a center of the ferrule 20, i.e., an equal distance from the four side surfaces 20SSA to 20SSD. The optical fiber 12 matches a central axis of the driving section 25 by being only inserted into the through hole H20.

The optical fiber scanning apparatus 10 is easily manufactured because the optical fiber 12 need not be processed. The endoscope 9 including the optical fiber scanning apparatus 10 can perform stable scanning, and is easily manufactured.

In other words, in the optical fiber scanning apparatus 10, the optical fiber 12 has a configuration in which the directions (the X-axis direction and the Y-axis direction) perpendicular to the optical axis are the same. However, lengths from the free end 12F1 to the fixed end is LY in the Y-axis direction (first direction) and LX in the X-axis direction (second direction). In other words, (LY=LX+D). Note that it goes without saying that the same effect is produced even if a formation direction of the groove T20 is the first direction (X-axis direction), i.e., (LX=LY+D).

Although the difference dFR between the resonance frequencies required to perform stable scanning irradiation differs depending on a specification of the optical fiber scanning apparatus 10, the resonance frequencies preferably differ by 0.2% or more, and particularly preferably differ by 0.5% or more, for example.

In the Lissajous scanning, an upper limit of the frequency of the Y-axis driving signal is less than ((Y-axis resonance frequency FR1)+(0.5 dFR)), and is preferably less than ((Y-axis resonance frequency FR1)+(0.25 dFR)). A lower limit of the frequency of the Y-axis driving signal is preferably (0.9×(Y-axis resonance frequency FR1)) or more to efficiently drive the optical fiber 12.

Similarly, a lower limit of the frequency of the X-axis driving signal is more than ((X-axis resonance frequency FR2)−(0.5 dFR)), and is preferably more than ((Y-axis resonance frequency FR2)−(0.25 dFR)). An upper limit of the frequency of the X-axis driving signal is preferably (1.1×(X-axis resonance frequency FR2)) or less to efficiently drive the optical fiber 12.

If a scanning method is the Lissajous scanning, the difference dFR between the resonance frequency FR1 in the first direction and the resonance frequency FR2 in the second direction of the optical fiber 12 is preferably kN (Hz) (k is a natural number) in an endoscope which shoots a movie with a frame rate of N (fps) with the reflected light from the object to be observed illuminated with the illumination light.

For example, one still image is shot in 1/30 seconds in a movie with a frame rate of 30 fps. In other words, both one cycle of scanning in the first direction and one cycle of scanning in the second direction are 1/30 seconds. If the difference dFR between the resonance frequencies is a multiple of the frame rate N, e.g., 30 Hz, 60 Hz, or 90 Hz, a start time and an end time of the one cycle of the scanning in the first direction and a start time and an end time of an N-th cycle of the scanning in the second direction match each other.

Note that the difference dFR between the resonance frequency FR1 and the resonance frequency FR2 is adjusted depending on the depth D of the groove T20. In other words, the larger the depth D is, the larger the difference dFR between the resonance frequencies becomes. Note that solder or a resin adhesive may be disposed in a gap between a bottom portion of the groove T20 and the through hole H20 and an outer main surface of the optical fiber 12. If a fillet is formed of solder or the like on a side surface of the optical fiber 12, a distal end portion of the fillet is considered as the depth D of the groove T20.

<Modifications to First Embodiment>

Respective optical fiber scanning apparatuses according to modifications to the first embodiment are similar to and have the same effect as the effect of the optical fiber scanning apparatus 10. Thus, components having the same functions are assigned the same reference numerals, and description of the components is omitted.

<Modification 1 to First Embodiment>

Figure 6:
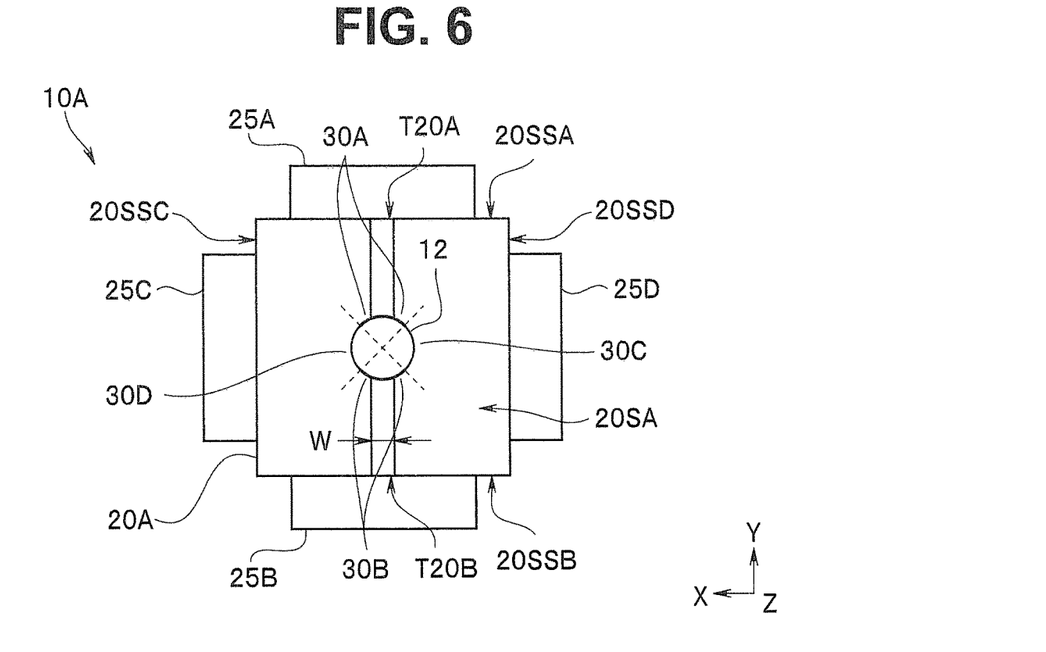
FIG. 6 is a front view of a principal part of an optical fiber scanning apparatus according to a modification 1 to the first embodiment.

In an optical fiber scanning apparatus 10A according to a modification 1 to the first embodiment illustrated in FIG. 6, a width W of two grooves T20A and T20B formed on a distal end surface 20SA of a ferrule 20A is less than an outer diameter of an optical fiber 12. Accordingly, a physical length L of a vibration section from a free end 12F1 to a fixed end 12F2 of the optical fiber 12 is the same in a Y-axis direction (first direction) and an X-axis direction (second direction). However, an "effective length LE" of the vibration section differs so that a resonance frequency FR differs in the Y-axis direction and the X-axis direction, as described below.

In the optical fiber scanning apparatus 10A, the optical fiber 12 is fixed by facing upper and lower wall surfaces of the ferrule 20A in the Y-axis direction (first direction), and sections constituting the wall surfaces are respectively considered as first fixing sections 30A and 30B. Similarly, the optical fiber 12 is fixed by facing right and left wall surfaces of the ferrule 20A in the X-axis direction (second direction), and sections constituting the wall surfaces are respectively considered as second fixing sections 30C and 30D. In other words, the optical fiber 12 is sandwiched between the pair of first fixing sections 30A and 30B and fixed in the first direction, and is sandwiched between the pair of second fixing sections 30C and 30D and fixed in the second direction.

Note that both the first fixing sections 30A and 30B and the second fixing sections 30C and 30D are each a part of the ferrule 20A composed of nickel, and is composed of the same material (nickel).

A space by the groove T20 exits at a center of each of respective abutment surfaces between the optical fiber 12 and the first fixing sections 30A and 30B which fix the Y-axis direction of the optical fiber 12. In other words, since the grooves T20A and T20B are formed, each of the abutment surfaces between the first fixing sections 30A and 30B and the optical fiber 12 is divided into two with the groove T20 as its center. Accordingly, the abutment surfaces between the first fixing sections 30A and 30B and the optical fiber 12 differ in shape from and are smaller in area than respective abutment surfaces between the second fixing sections 30C and 30D and the optical fiber 12.

In the optical fiber 12, a resonance frequency FR1 in the Y-axis direction (first direction) is lower than a resonance frequency FR2 in the X-axis direction (second direction). This is considered to be because the "effective length LE" in the Y-axis direction is larger than the "effective length LE" in the X-axis direction, although the actual vibration length (physical length) L from the free end 12F1 to the fixed end 12F2 of the optical fiber 12 is the same in the Y-axis direction and the X-axis direction.

In other words, such an effect that the first fixing sections 30A and 30B and the second fixing sections 30C and 30D differ in a shape of an abutment portion abutting on the optical fiber 12, and thus differ in the "effective length LE" is produced. More specifically, a fixing force (binding force) of the first fixing sections 30A and 30B fixing the optical fiber 12 is smaller than a fixing force of the second fixing sections 30C and 30D. Thus, an effective length LE1 in the Y-axis direction may conceivably be larger than an effective length LE2 in the X-axis direction. The larger the width W of the groove T20 is, the smaller the fixing force becomes, and thus the larger a difference dFR between the resonance frequencies becomes.

The optical fiber scanning apparatus 10A is superior in reliability for long-term use to the optical fiber scanning apparatus 10 because an outer peripheral surface of the optical fiber 12 may not rub against a wall surface of the groove T20 to be worn, unlike the optical fiber scanning apparatus 10, when the optical fiber 12 vibrates in the first direction (Y-axis direction).

Since the entire outer periphery of the optical fiber 12 is fixed by the first fixing sections 30A and 30B and the second fixing sections 30C and 30D at the fixed end 12F2, the vibration length is the same in the X-axis direction and the Y-axis direction. Thus, in the optical fiber scanning apparatus 10A, control to two-dimensionally scan the free end 12F1 of the optical fiber 12 by the control unit 5 is easy.

<Modification 2 to First Embodiment>

Figure 7:
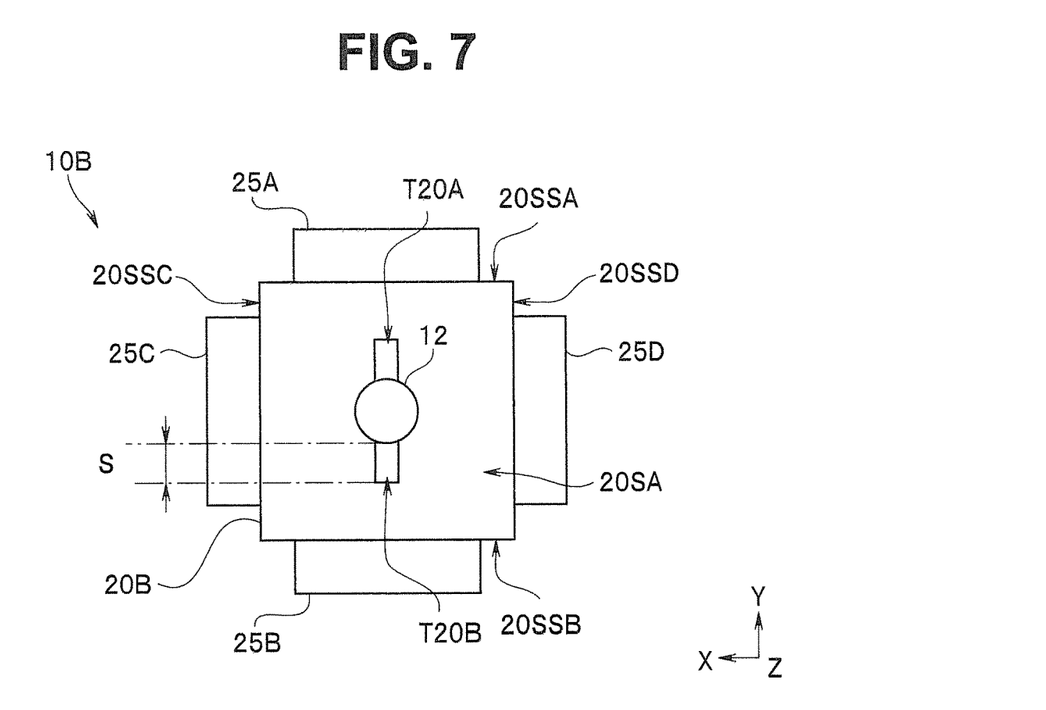
FIG. 7 is a front view of a principal part of an optical fiber scanning apparatus according to a modification 2 to the first embodiment.

As illustrated in FIG. 7, in an optical fiber scanning apparatus 10B according to a modification 2 to the first embodiment, a length S of grooves T20A and T20B is smaller than the length in the optical fiber scanning apparatus 10A. In other words, the groove T20 does not reach a side surface 20SS of a ferrule 20B. However, even if the length S of the groove T20 is small, a shape of an abutment portion differs in a first direction and a second direction. Thus, the optical fiber scanning apparatus 10B has the same effect as the effect of the optical fiber scanning apparatus 10A. Note that in the optical fiber scanning apparatus 10, the groove T20 needs not reach the side surface 20SS of the ferrule 20.

The two grooves T20A and T20B which have reached the side surface 20SS of the ferrule 20, like in the optical fiber scanning apparatus 10, can be simultaneously formed using a dicing saw or the like. Accordingly, the groove T20 extending to the side surface 20SS of the ferrule 20, that is, the groove T20 having an opening on the side surface 20SS of the ferrule 20 is more preferable than a groove having a small length S.

Second Embodiment

An optical fiber scanning apparatus 10C according to a second embodiment is similar to and has the same effect as the effect of the optical fiber scanning apparatus 10. Thus, components having the same functions are assigned the same reference numerals, and description of the components is omitted.

Figure 8:
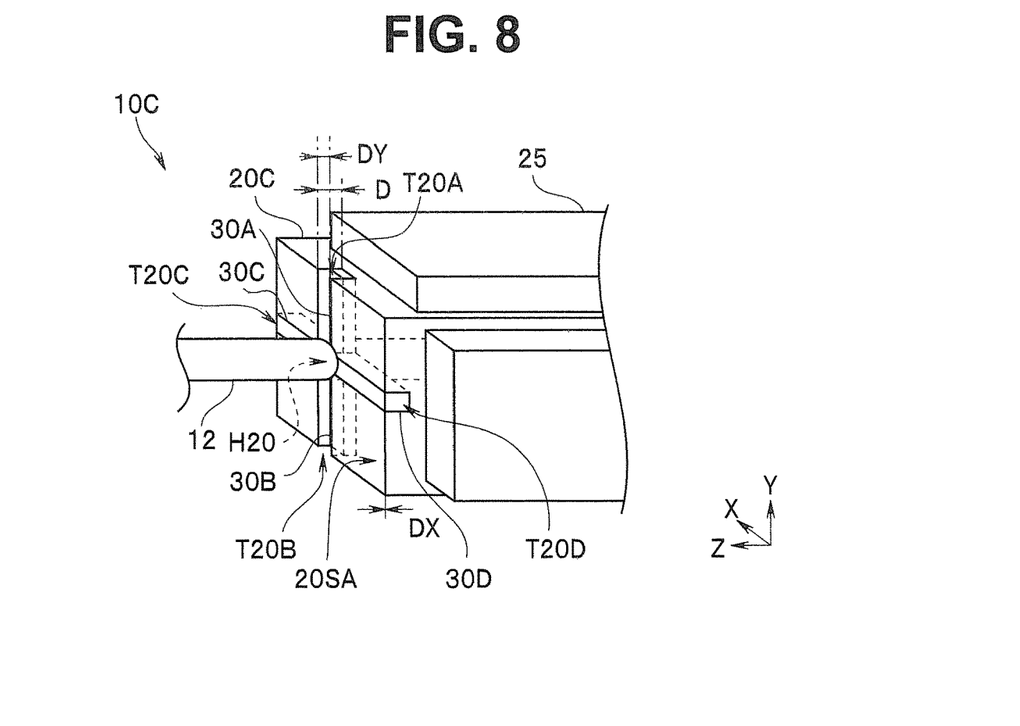
FIG. 8 is a perspective view of a principal part of an optical fiber scanning apparatus according to a second embodiment.

In an optical fiber scanning apparatus 10C illustrated in FIG. 8, four grooves T20A to T20D each having a depth D having an opening on a wall surface of a through hole H20 are formed to be rotationally symmetric around the through hole H20 on a distal end surface 20SA of a ferrule 20C. The groove T20A and the groove T20B are arranged to face each other on opposite sides of the through hole H20. Thus, the grooves T20A and T20B, together with the through hole H20, apparently constitute a consecutive single groove. Similarly, the grooves T20C and T20C, together with the through hole H20, constitute a consecutive single groove. A long-axis direction of the grooves T20A and T20B is a first direction (Y-axis direction), a long-axis direction of the grooves T20C and T20D is a second direction (X-axis direction), and a depth direction of the grooves T20A to T20D is an optical axis direction.

Solder composing first fixing sections 30A and 30B is disposed in the pair of grooves T20A and T20B facing each other. However, the grooves T20A and T20B each having the depth D are not completely filled, respectively, with the first fixing sections 30A and 30B, and the grooves T20A and T20B each have a depth DY. On the other hand, the pair of grooves T20C and T20D facing each other are respectively filled and embedded with solder composing second fixing sections 30C and 30D. In other words, the grooves T20C and T20D each have a depth DX of zero.

Accordingly, a length from a free end 12F1 to a fixed end differs in the Y-axis direction (first direction) and the X-axis direction (second direction). In other words, a length LY in the Y-axis direction (first direction) is larger than a length LX in the X-axis direction (second direction), and (LY=LX+DY). Note that if the depth DY and the depth DX differ from each other, the groove T20C and T20D each having the depth D need not be completely filled, respectively, with the second fixing sections 30C and 30D, and solder may not be disposed in the first fixing sections 30A and 30B.

As described above, in the optical fiber scanning apparatus 10C, at least one of the pair of first fixing sections 30A and 30B which sandwich and fix the optical fiber 12 in the first direction and the pair of second fixing sections 30C and 30D which sandwich and fix the optical fiber 12 in the second direction is composed of solder as the fixing sections respectively disposed in the pair of grooves T20A and T20B facing each other among the four grooves T20A to T20D each having the opening on the wall surface of the through hole H20 and formed to be rotationally symmetric around the through hole H20 as the center. Resin may be disposed in place of solder in the groove T20.

In the optical fiber scanning apparatus 10C, the length LY in the Y-axis direction (first direction) and the length LX in the X-axis direction (second direction) differ from each other due to solder disposed in the groove T20. Thus, the resonance frequencies FR1 and FR2 differ from each other.

<Modifications to Second Embodiment>

Respective optical fiber scanning apparatuses 10D, 10E according to modifications to the second embodiment are similar to and have the same effect as the effect of the optical fiber scanning apparatus 10C. Thus, components having the same functions are assigned the same reference numerals, and description of the components is omitted.

<Modification 1 to Second Embodiment>

Figure 9:
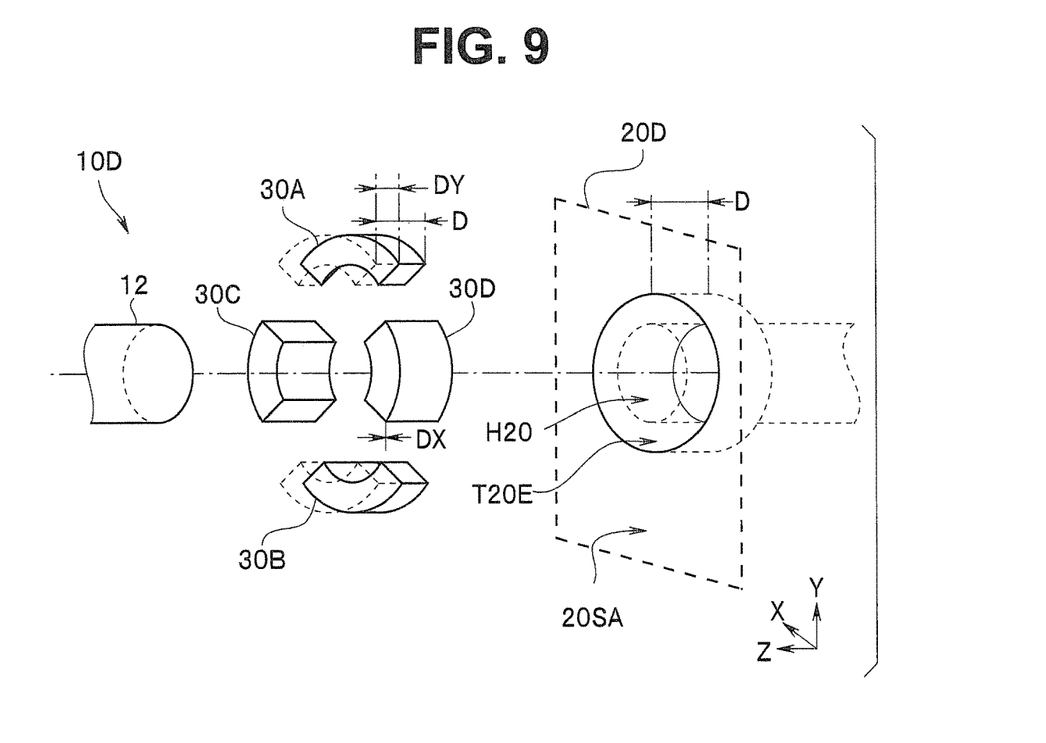
FIG. 9 is an exploded view of a principal part of an optical fiber scanning apparatus according to a modification 1 to the second embodiment.

In an optical fiber scanning apparatus 10D according to a modification 1 to the second embodiment illustrated in FIG. 9, a groove T20E is a donut-shaped recess portion formed over an entire outer periphery of a through hole H20. In other words, a diameter of the through hole H20 on a distal end surface 20SA of a ferrule 20D is apparently large.

First fixing sections 30A and 30B and second fixing sections 30C and 30D are each composed of solder and are designed to match a shape of the groove T20E and an outer diameter of an optical fiber 12, and are combined to be embedded in the groove T20E, to fix the optical fiber 12.

The first fixing sections 30A and 30B do not completely fill the groove T20E having a depth D, and a depth of the groove T20E in the first direction (Y-axis direction) is DY. On the other hand, the second fixing sections 30C and 30D do not completely fill the groove T20E having the depth D, and a depth DX of the groove T20E in the second direction (X-axis direction) is zero.

In other words, even if the four grooves perpendicular to one another in the optical fiber scanning apparatus 10C are replaced with the donut-shaped groove T20E, the optical fiber scanning apparatus 10D has the same effect as the effect of the optical fiber scanning apparatus 10C.

Note that although an outer periphery of the groove T20E in the optical fiber scanning apparatus 10D is circular, the outer periphery may be rectangular or polygonal.

<Modification 2 to Second Embodiment>

Figure 10:
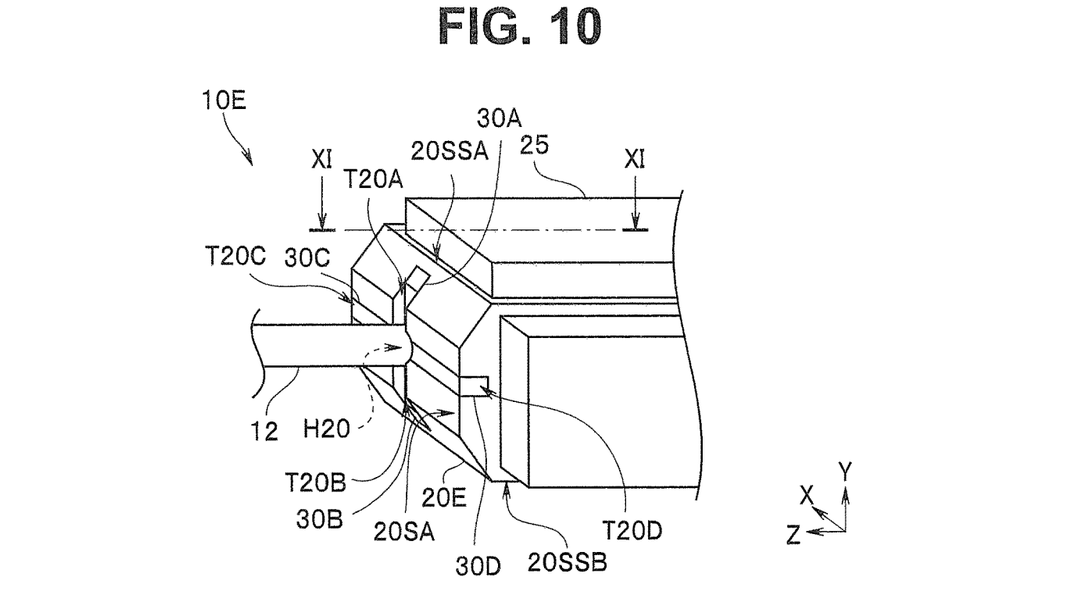
FIG. 10 is a perspective view of a principal part of an optical fiber scanning apparatus according to a modification 2 to the second embodiment.
Figure 11:
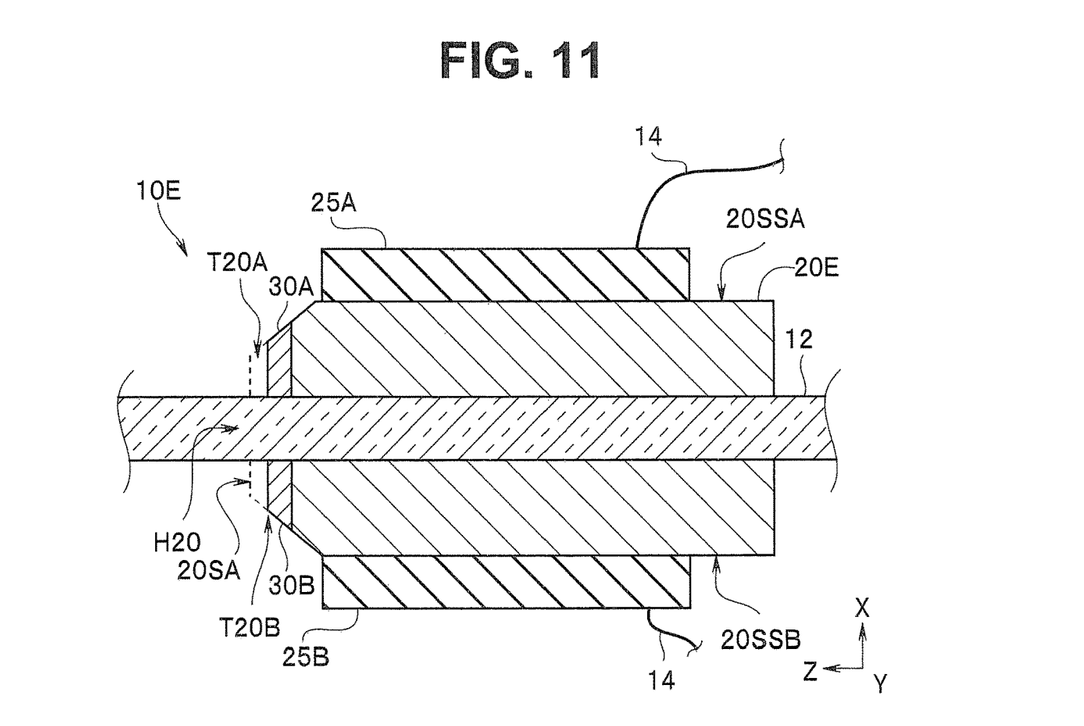
FIG. 11 is a cross-sectional view along a line XI-XI illustrated in FIG. 10 of the principal part of the optical fiber scanning apparatus according to the modification 2 to the second embodiment.

In an optical fiber scanning apparatus 10E in a modification 2 to the second embodiment illustrated in FIGS. 10 and 11, corner portions respectively formed between a distal end surface 20SA and side surfaces 20SSA and 20SSB of a ferrule 20E are chamfered.

In the optical fiber scanning apparatus 10E, grooves T20A and T20B each having a depth D are not completely filled, respectively, with fixing sections 30, and the grooves T20A and T20B each have a depth DY, like in the optical fiber scanning apparatus 10C. On the other hand, a pair of grooves T20C and T20D facing each other is filled and embedded with solder as the fixing sections 30.

A length LY in a Y-axis direction (first direction) is larger than a length LX in an X-axis direction (second direction), and (LY=LX+DY). Accordingly, a resonance frequency FR1 of the optical fiber 12 is lower than a resonance frequency FR2 of the optical fiber 12. Further, in the optical fiber scanning apparatus 10E, corner portions of side surfaces 20SSA and 20SSB in the Y-axis direction (first direction) in which the resonance frequency is low are chamfered. Thus, the resonance frequency FR1 is even lower than the resonance frequency FR1 in the optical fiber scanning apparatus 10C.

It is presumed that this is because in the optical fiber scanning apparatus 10E in which the corner portions are chamfered, an "effective length LE" of the optical fiber 12 which affects the resonance frequency FR in a direction in which the corner portions are chamfered is larger than the "effective length LE" in the optical fiber scanning apparatus 10C.

In the optical fiber scanning apparatus 10E, more stable scanning can be performed because a difference dFR between the resonance frequencies is larger than the difference dFR between the resonance frequencies in the optical fiber scanning apparatus 10C.

Third Embodiment

An optical fiber scanning apparatus 10F according to a third embodiment is similar to and has the same effect as the effects of the optical fiber scanning apparatus 10 and the like. Thus, components having the same functions are assigned the same reference numerals, and description of the components is omitted.

Figure 12:
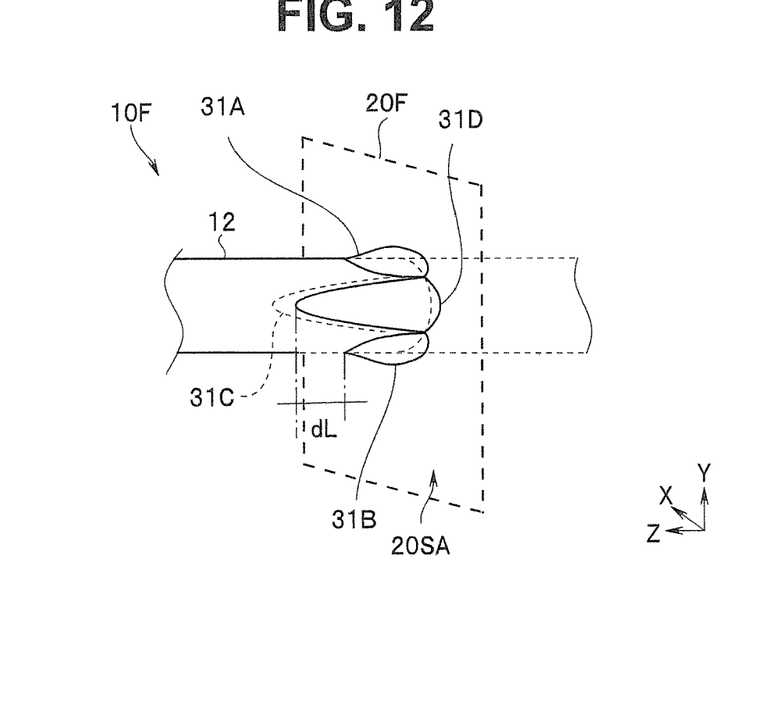
FIG. 12 is a perspective view of a principal part of an optical fiber scanning apparatus according to a third embodiment.
Figure 13:
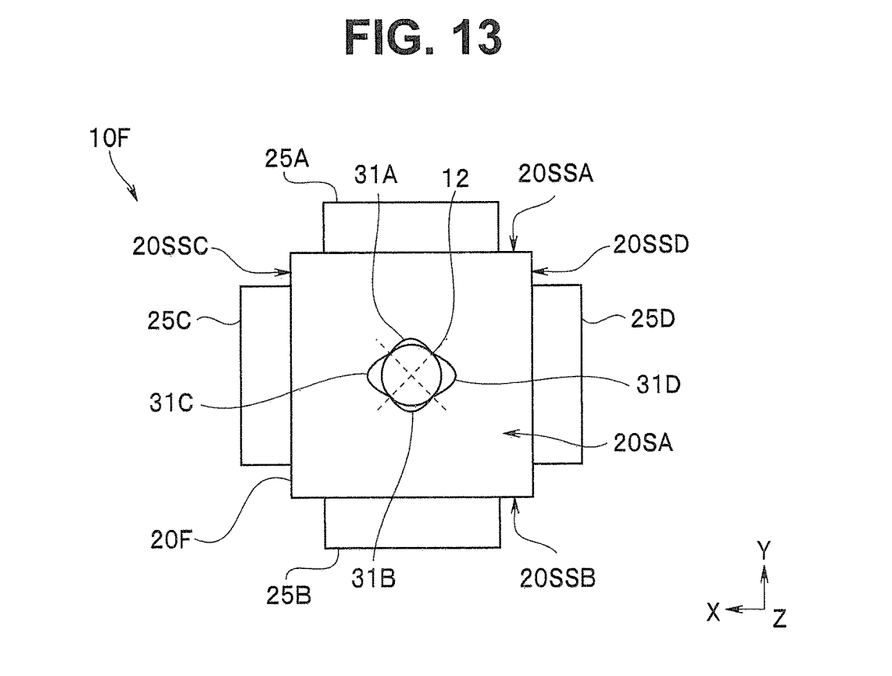
FIG. 13 is a front view of the principal part of the optical fiber scanning apparatus according to the third embodiment.

In an optical fiber scanning apparatus 10F illustrated in FIGS. 12 and 13, an optical fiber 12 is fixed by fixing sections 31 disposed on a distal end surface 20SA of a ferrule 20F.

An outer periphery of the optical fiber 12 is fixed by first fixing sections 31A and 31B each composed of solder in a first direction (Y-axis direction), and is also fixed by second fixing sections 31C and 31D each composed of solder in a second direction (X-axis direction). In other words, the first fixing sections 31A and 31B and the second fixing sections 31C and 31D are each composed of a fillet extending to an outer peripheral surface of the optical fiber 12 from the distal end surface 20SA of the ferrule 20F. Note that the outer peripheral surface of the optical fiber 12 is coated with gold which can be solder-bonded.

The fillets respectively composing the first fixing sections 31A and 31B are shorter by dL than the fillets respectively composing the second fixing sections 31C and 31D. Accordingly, for a length from a free end to a fixed end of the optical fiber 12, a length LY in the Y-axis direction (first direction) is larger than a length LX in the X-axis direction (second direction), and (LY=LX+dL). Accordingly, a resonance frequency FR1 is lower than a resonance frequency FR2.

Note that although a length of the fillet can be adjusted by an amount of solder, a length of a gold film disposed on an outer surface of the optical fiber 12 may be changed, or a resist film may be disposed such that solder is not disposed. The fillet may be composed of resin in place of solder.

The optical fiber scanning apparatus 10F is more easily manufactured than the optical fiber scanning apparatus 10 or the like because a groove needs not be formed in the ferrule 20F.

Note that in the foregoing description, the optical fiber scanning apparatus 10 using the piezoelectric driving method in which the driving section includes the piezoelectric elements 25, for example, has been described. However, the optical fiber scanning apparatus according to the embodiment may use an electromagnetic driving method in which the driving section includes a magnet. In the electromagnetic driving method, an alternating magnetic field is applied from outside to an optical fiber to which a magnetic body (magnet) is attached. In the optical fiber scanning apparatus using the electromagnetic driving method, a holding section (ferrule) may be not a rectangular parallelepiped but a circular column or a polygonal column having a polygon with five or more sides and angles as its base.

The first fixing section and the second fixing section may be respectively composed of different materials. For example, the first fixing sections 31A and 31B illustrated in FIGS. 12 and 13 may be composed of solder, and the second fixing sections 31C and 31D may be composed of resin.

Needless to say, an endoscope including the optical fiber scanning apparatus 10A or 10B according to the modification to the first embodiment, the optical fiber scanning apparatus 10C according to the second embodiment, the optical fiber scanning apparatus 10D or 10E according to the modification to the second embodiment, or the optical fiber scanning apparatus 10F according to the third embodiment has an effect of the endoscope 9 according to the first embodiment, and further has an effect of the optical fiber scanning apparatus included in the endoscope.

The present invention is not limited to each of the above-described embodiments and modifications, but various changes, combinations, and applications are possible without departing from the scope and spirit of the invention.

What is claimed is:

1. An optical fiber scanning apparatus comprising:
   an optical fiber comprising a free end, the optical fiber being configured to emit illumination light in an optical axis direction, the free end being configured to vibrate in a first direction and a second direction perpendicular to the first direction;
   a ferrule including a through hole through which the optical fiber is inserted, the ferrule including a pair of first supports and a pair of second supports, the pair of first supports fixing the optical fiber in the first direction and the pair of second supports fixing the optical fiber in the second direction such that the optical fiber is cantilevered from the pair of first supports in the first direction and the optical fiber is cantilevered from the pair of second supports in the second direction; and
   piezoelectric elements or magnets configured to vibrate the optical fiber,
   wherein the ferrule comprising a groove formed on a distal end surface of the ferrule, the groove having a bottom surface and side walls extending from the bottom surface, the bottom surface of the groove having an opening, the opening communicating with the through hole, the groove extending in the first direction such that the sidewalls form each of the pair of second supports, and a width of the groove between the sidewalls is slightly larger than the outer diameter of the optical fiber; and
   a first distance between the free end and the pair of first supports in an optical axis direction is different from a second distance between the free end and the pair of second supports in the optical axis direction.

2. The optical fiber scanning apparatus according to claim 1, wherein the pair of first supports and the pair of second supports are formed of a same material.

3. An optical fiber scanning apparatus comprising:
   an optical fiber comprising a free end, the optical fiber being configured to emit illumination light in an optical axis direction, the free end being configured to vibrate in a first direction and a second direction perpendicular to the first direction;
   a ferrule including a through hole through which the optical fiber is inserted, the ferrule including a pair of first supports and a pair of second supports, the pair of first supports fixing the optical fiber in the first direction and the pair of second supports fixing the optical fiber in the second direction such that the optical fiber is cantilevered from the pair of first supports in the first direction and the optical fiber is cantilevered from the pair of second supports in the second direction; and
   piezoelectric elements or magnets configured to vibrate the optical fiber,
   wherein the ferrule comprising a groove formed on a distal end surface of the ferrule, the groove having a bottom surface and side walls extending from the bottom surface, the bottom surface of the groove having an opening, the opening communicating with the through hole, the groove extending in the first direction such that the sidewalls form each of the pair of second supports, and a width of the groove between the sidewalls is slightly larger than the outer diameter of the optical fiber; and
   the width of the groove is not more than 105% of the outer diameter of the optical fiber.

4. An endoscope comprising:
   an insertion section configured to be inserted into a lumen; and
   the optical fiber scanning apparatus according to claim 1 disposed in a distal end portion of the insertion section.

5. The endoscope according to claim 4, wherein
   a movie with a frame rate of N (fps) is shot with reflected light from an object to be observed illuminated with the illumination light scanned by a Lissajous method, and
   a difference between a resonance frequency in the first direction and a resonance frequency in the second direction of the optical fiber is kN (Hz) (k is a natural number).

6. An optical fiber scanning apparatus comprising:
   an optical fiber comprising a fixed end and a free end, a movement of the fixed end being restricted in a direction of vibration of the optical fiber, movement of the free end is not restricted in the direction of vibration, the optical fiber being configured to emit illumination light from the free end;
   an actuator configured to move the free end in a first direction and in a second direction perpendicular to the first direction by vibrating the optical fiber; and
   a ferrule including a fixing section, the fixing section comprising:
- a through hole through which the optical fiber is inserted;
- a pair of first supports configured to restrict a movement of the optical fiber in the first direction with respect to vibration in the first direction when the optical fiber is vibrated; and
- a pair of second supports disposed at a position where an effective length from the free end of the optical fiber to the pair of second supports is different from an effective length from the free end to the pair of first supports, the pair of second supports being configured to restrict a movement of the optical fiber in the second direction with respect to vibration in the second direction, wherein the ferrule comprising a groove formed on a distal end surface of the ferrule, the groove having a bottom surface and side walls extending from the bottom surface, the bottom surface of the groove having an opening, the opening communicating with the through hole, the groove extending in the first direction such that the sidewalls form each of the pair of second supports, and a width of the groove between the sidewalls is slightly larger than the outer diameter of the optical fiber; and a first distance between the free end and the pair of first supports in an optical axis direction is different from a second distance between the free end and the pair of second supports in the optical axis direction.

7. An optical fiber scanning apparatus comprising:
an optical fiber comprising a free end from which illumination light is emitted in an optical axis direction, the free end being configured to move by vibration;
an actuator configured to move the free end in a first direction and in a second direction perpendicular to the first direction by vibrating the optical fiber; and
a ferrule including a fixing section,
the fixing section comprising:
- a through hole through which the optical fiber is inserted in the optical axis direction;
- a pair of first supports configured to restrict a movement of the optical fiber in the first direction with respect to the vibration; and
- a pair of second supports configured to restrict a movement of the optical fiber in the second direction with respect to the vibration, wherein a length between the free end and the fixing section changes along the circumference of the optical fiber at the fixed end, and the ferrule comprising a groove formed on a distal end surface of the ferrule, the groove having a bottom surface and side walls extending from the bottom surface, the bottom surface of the groove having an opening, the opening communicating with the through hole, the groove extending in the first direction such that the sidewalls form each of the pair of second supports, and a width of the groove between the sidewalls is slightly larger than the outer diameter of the optical fiber; and a first distance between the free end and the pair of first supports in an optical axis direction is different from a second distance between the free end and the pair of second supports in the optical axis direction.

8. An optical fiber scanning apparatus comprising:
an optical fiber comprising a fixed end and a free end for emitting illumination light in an optical axis direction, the fixed end being fixed, the free end being configured to vibrate in a first direction and a second direction perpendicular to the first direction;
a ferrule including a through hole through which the optical fiber is inserted and including a fixing section having a pair of first fixing sections and a pair of second fixing sections which respectively fix the fixed end of the optical fiber; and
piezoelectric elements or magnets configured to vibrate the optical fiber, wherein the optical fiber is fixed in the first direction by being sandwiched between the pair of first fixing sections, and is fixed in the second direction by being sandwiched between the pair of second fixing sections, and a shape of a contact area of the fixing section abutting the optical fiber changes along the optical axis direction, and the ferrule comprising a groove formed on a distal end surface of the ferrule, the groove having a bottom surface and side walls extending from the bottom surface, the bottom surface of the groove having an opening, the opening communicating with the through hole, the groove extending in the first direction such that the sidewalls form each of the pair of second supports, and a width of the groove between the sidewalls is slightly larger than the outer diameter of the optical fiber; and wherein a first distance between a free end and the pair of first fixing sections in an optical axis direction is different from a second distance between the free end and the pair of second fixing sections in the optical axis direction.

9. The optical fiber scanning apparatus according to claim 8, wherein a first contact area of the pair of second fixing sections extends linearly in a longitudinal direction of the optical fiber and a second contact area of the pair of second fixing portions extends circumferentially around an outer circumferential surface of the optical fiber.

10. The optical fiber scanning apparatus according to claim 6, wherein the width of the groove is not more than 105% of the outer diameter of the optical fiber.

11. The optical fiber scanning apparatus according to claim 7, wherein the width of the groove is not more than 105% of the outer diameter of the optical fiber.

12. The optical fiber scanning apparatus according to claim 8, wherein the width of the groove is not more than 105% of the outer diameter of the optical fiber.

* * * * *